US012640269B2

(12) United States Patent
Le Tallec et al.

(10) Patent No.: US 12,640,269 B2
(45) Date of Patent: May 26, 2026

(54) INTERACTIVE SYSTEM FOR ASSISTING WITH A VETERINARY EVALUATION PROCEDURE

(71) Applicant: Ceva Santé Animale, Libourne (FR)

(72) Inventors: Bertrand Le Tallec, Libourne (FR);
François Roulleau, Libourne (FR);
Jean Leorat, Libourne (FR)

(73) Assignee: CEVA SANTE ANIMALE, Libourne (FR)

( * ) Notice: Subject to any disclaimer, the term of this patent is extended or adjusted under 35 U.S.C. 154(b) by 50 days.

(21) Appl. No.: 18/276,197

(22) PCT Filed: Feb. 7, 2022

(86) PCT No.: PCT/EP2022/052869
§ 371 (c)(1),
(2) Date: Aug. 7, 2023

(87) PCT Pub. No.: WO2022/171566
PCT Pub. Date: Aug. 18, 2022

(65) Prior Publication Data
US 2024/0304326 A1     Sep. 12, 2024

(30) Foreign Application Priority Data

Feb. 10, 2021     (EP) ..................................... 21156213

(51) Int. Cl.
*G16H 50/20*          (2018.01)
*G16H 10/20*          (2018.01)
*G16H 15/00*          (2018.01)
(52) U.S. Cl.
CPC ............. *G16H 50/20* (2018.01); *G16H 10/20* (2018.01); *G16H 15/00* (2018.01)

(58) Field of Classification Search
CPC ........ G16H 50/20; G16H 10/20; G16H 15/00; G16H 70/00; G16H 80/00
See application file for complete search history.

(56) References Cited

U.S. PATENT DOCUMENTS 4,130,881 A * 12/1978 Haessler ................ G16H 10/60
                                                                    705/3
9,779,631 B1 * 10/2017 Miller .................... G16H 15/00
                           (Continued)

FOREIGN PATENT DOCUMENTS

WO      WO-2020264533 A1 * 12/2020 ............. G06Q 10/10

OTHER PUBLICATIONS

Watson et al., A survey of knowledge and use of telehealth among veterinarians, 2019, BMC Veterinary Research, pp. 1-8. ( Year: 2019).*

*Primary Examiner* — Christopher L Gilligan
(74) *Attorney, Agent, or Firm* — Wood, Phillips, Katz, Clark & Mortimer

(57) ABSTRACT

The invention relates to an interactive system (1) for assisting with a veterinary evaluation procedure, comprising: a connected device (2) able to be worn on the head of a veterinarian and equipped with a system for acquiring and emitting audio (23, 24) and with a wireless communication system (27); a mobile terminal (3) equipped with a display (31), with an interface (31) and with a controller (A) arranged to display a consultation questionnaire on the display of the mobile terminal and to generate at least one comment (Cp) relative to a consultation being carried out by the veterinarian depending on at least one of the responses (RI) given to the questionnaire via the interface.

8 Claims, 7 Drawing Sheets

(56)  References Cited

U.S. PATENT DOCUMENTS

| | | | |
|---|---|---|---|
| 9,947,043 B2 * | 4/2018 | Neale ..................... | G06Q 40/00 |
| 12,086,563 B1 * | 9/2024 | Draelos ................ | G06F 40/186 |
| 2002/0116200 A1 * | 8/2002 | Cureton ................... | A01K 5/02 |
| | | | 348/E13.004 |
| 2012/0034583 A1 * | 2/2012 | Dujowich ............... | G09B 7/06 |
| | | | 434/219 |
| 2014/0222462 A1 * | 8/2014 | Shakil .................... | G16H 10/60 |
| | | | 705/3 |
| 2015/0332021 A1 * | 11/2015 | Godla ................... | G16H 10/60 |
| | | | 705/3 |
| 2019/0206134 A1 * | 7/2019 | Devam ................... | G06F 3/011 |
| 2019/0385711 A1 * | 12/2019 | Shriberg ............... | G16H 15/00 |
| 2020/0060240 A1 * | 2/2020 | Yajima ................... | A01K 13/00 |

* cited by examiner

[Fig. 1]
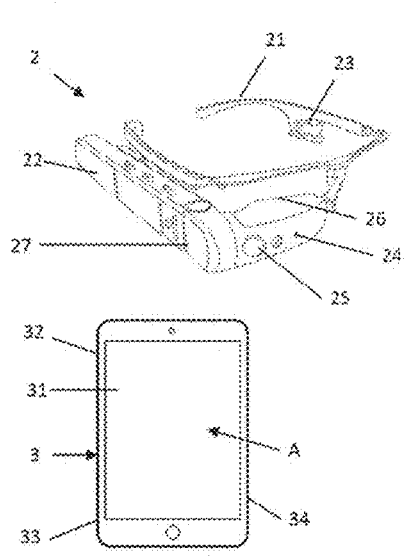
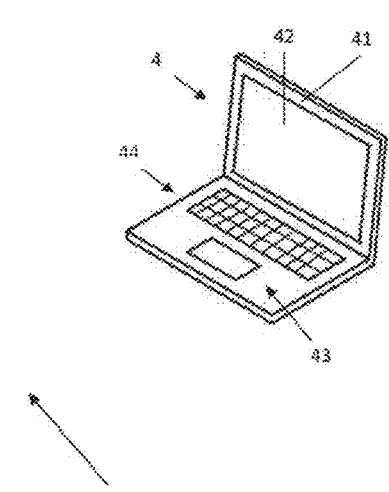
[Fig. 2]
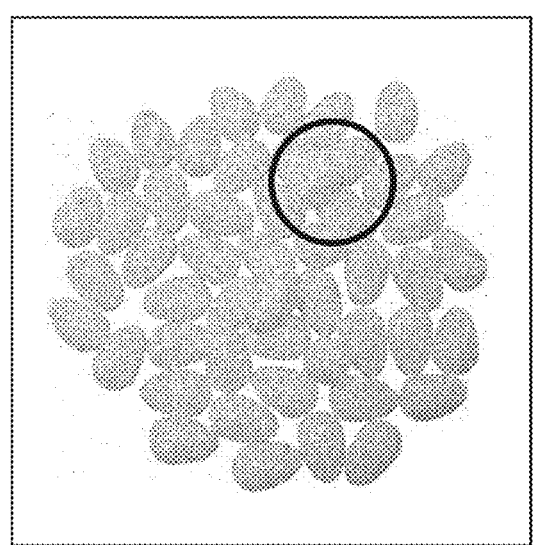

[Fig. 3]
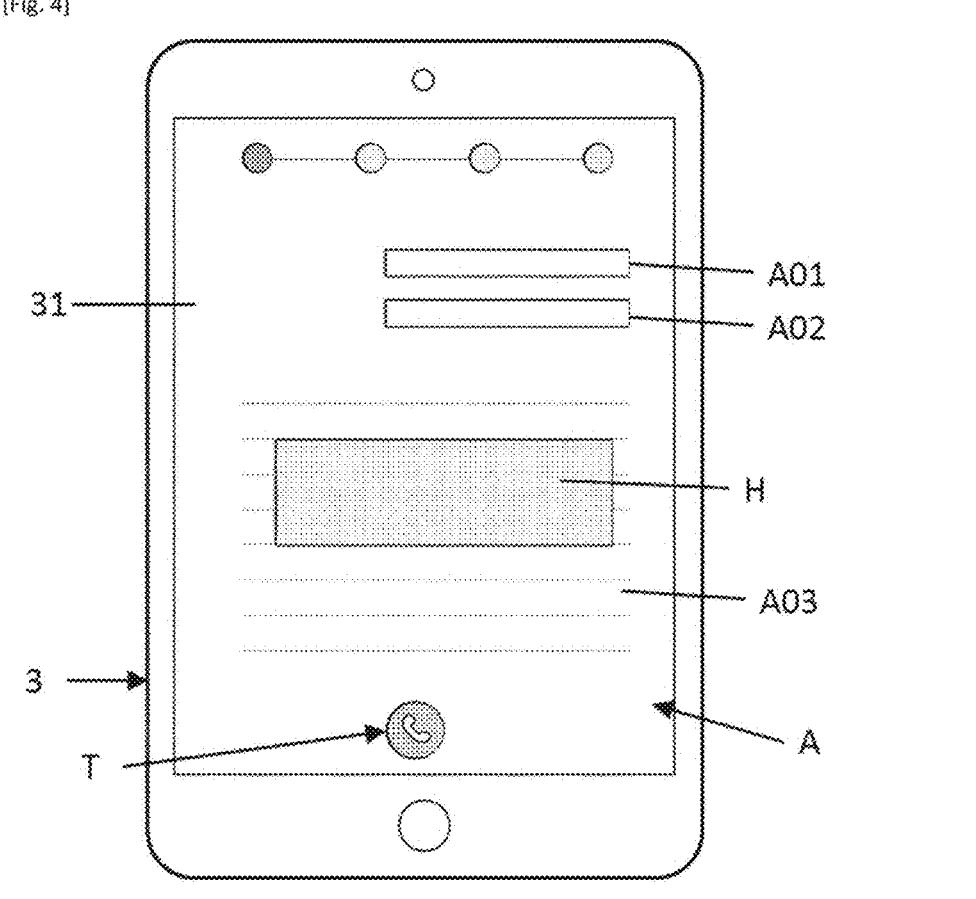
[Fig. 4]

[Fig. 5]
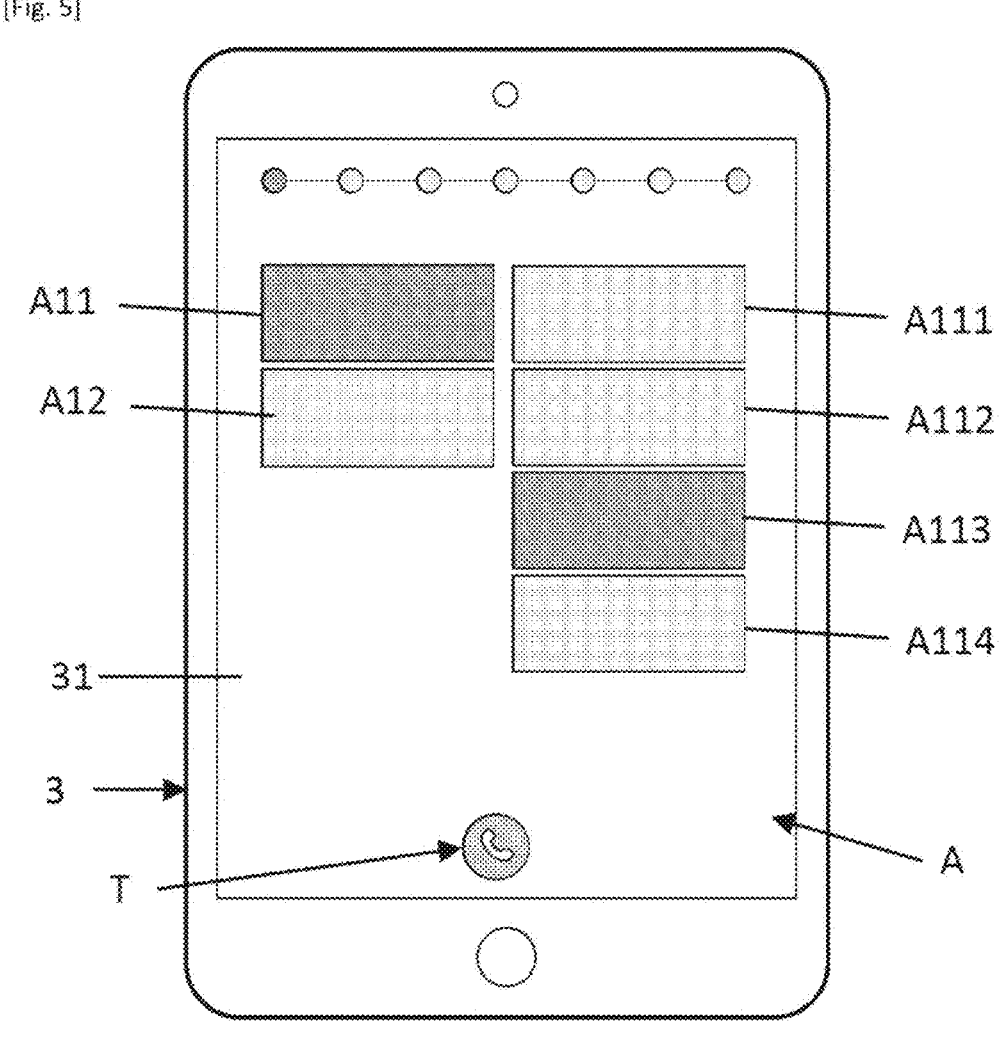

[Fig. 6]

[Fig. 7]
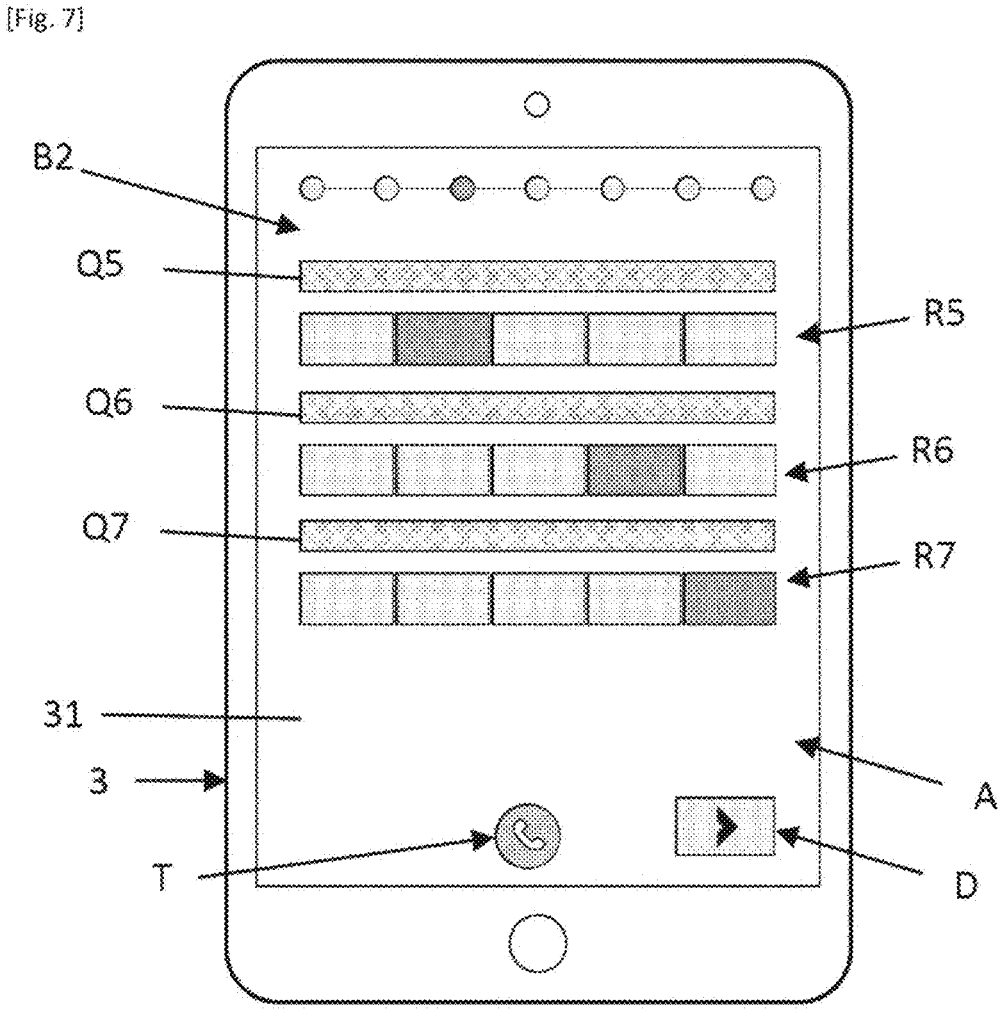

[Fig. 8]
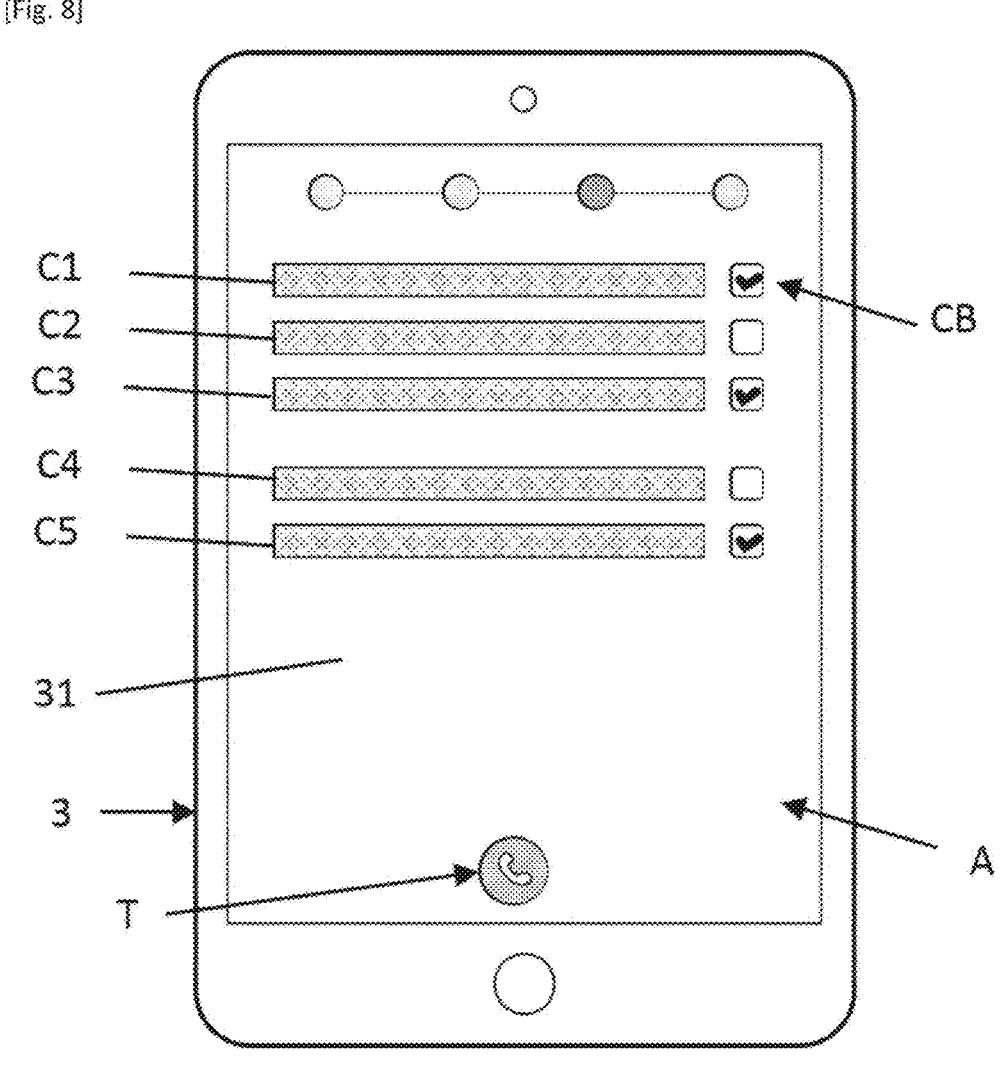

[Fig. 9]
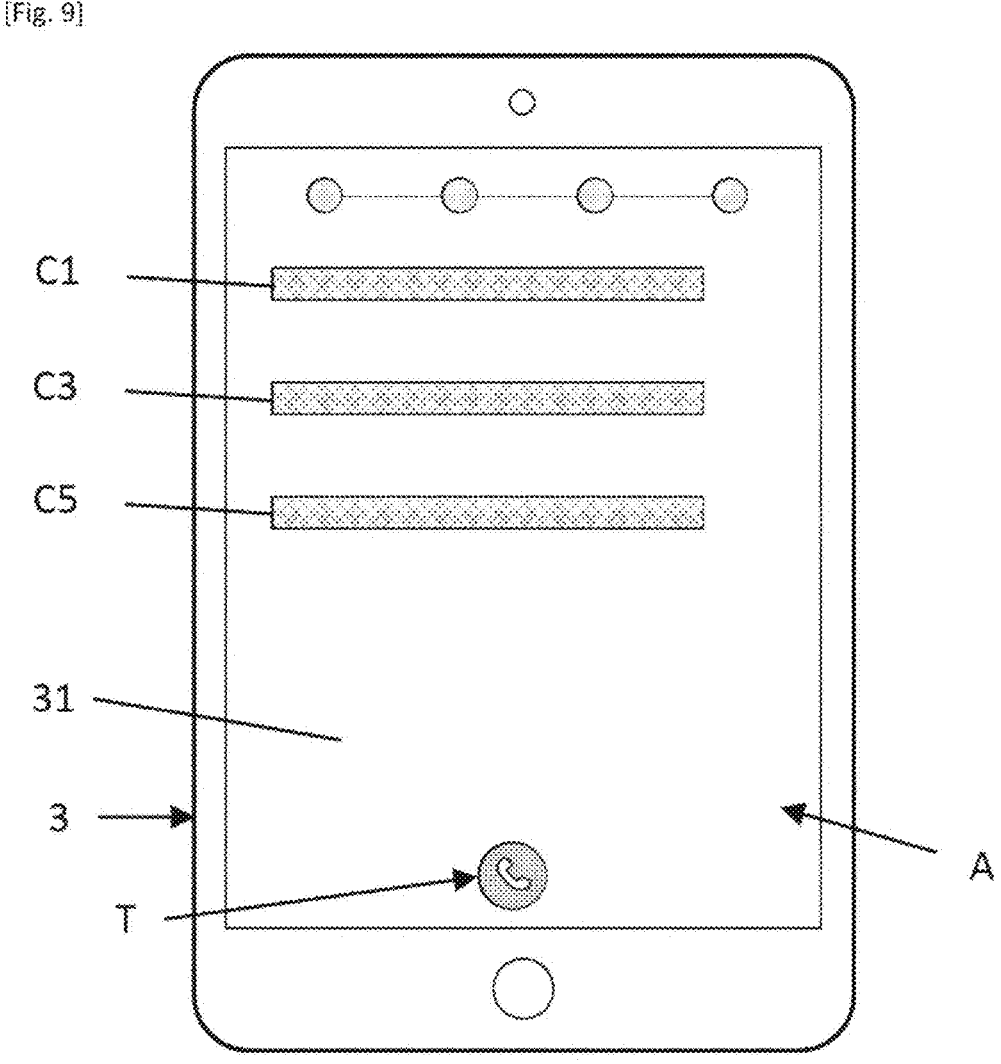

INTERACTIVE SYSTEM FOR ASSISTING WITH A VETERINARY EVALUATION PROCEDURE

FIELD OF THE INVENTION

The invention relates to the technical field of veterinary activities. More precisely, the invention relates to an interactive system for assisting with a veterinary evaluation procedure.

BACKGROUND OF THE INVENTION

In the veterinary services field, it is known to call on a veterinarian to organize a check-up, evaluation or diagnostic visit in industrial or non-industrial farming, or else in an agri-food operation. This is in particular the case when the farm or operation is faced with a sanitary or zootechnical problem, and particularly when disease is suspected in animals. For example, in the context of a poultry farm, this visit can in particular make it possible to diagnose the appearance of a disease within the flock such as a Newcastle Disease (also called "ND"), Infectious Bronchitis (also called "IB"), Infectious Laryngotracheitis (also called "ILT"), Infectious Bursal Disease (also called "IBD") or avian flu.

However, when organizing the visit, the veterinarian has little information regarding the reasons why he has been called out. Now, there may be multiple reasons, each of which can belong to a specific field or discipline such as, inter alia, animal science, infectious diseases, epidemiology, clinical pathology, biosafety, livestock management, or immunization, or even a particular branch of these fields and disciplines. This implies that the veterinarian, despite his multidisciplinary experience, may need specific expertise in order to conduct his evaluation. This is in particular the case when the farm or operation calls for a general veterinarian or a veterinarian in the early stages of his career. Additionally, the information available before the visit can cause a bias in his evaluation and prevent him from performing a multi-factor and multidisciplinary analysis. These points can be particularly critical in an industrial farm context, since a misdiagnosed or late-diagnosed pathology can cause an error or a treatment delay resulting in significant damage.

One solution could consist in organizing a joint visit of the veterinarian with an expert in the species. However, it is not always possible to organize a visit, within an acceptable time, by an expert having these required skills, on the one hand because of the increasing number of consultations with regard to the number of experts available and on the other hand because of the costs that such travel incurs.

There is thus a need for a solution allowing a veterinarian to carry out an in situ consultation on a farm, for check-up, evaluation or diagnostic purposes, and allowing them to call on specific expertise in order for the check-up, evaluation or diagnosis to be carried out as quickly and as reliably as possible.

The present invention falls in this context and aims to meet this need.

BRIEF SUMMARY OF THE INVENTION

For these purposes, the invention relates to an interactive system for assisting with a veterinary evaluation procedure, comprising:

a. a connected device able to be worn on the head of a veterinarian and equipped with a system for acquiring and emitting audio and with a wireless communication system;

b. a mobile terminal equipped with a display, with an interface and with a controller arranged to display a consultation questionnaire on the display of the mobile terminal and to generate at least one comment relative to a consultation being carried out by the veterinarian depending on at least one of the responses given to the questionnaire via the interface.

Owing to the invention, a veterinarian equipped on the one hand with the connected device and on the other hand with the mobile terminal can organize a visit to a farm. The connected device allows him to converse with a remote expert, who has the specific skills required for the purpose of his intervention. In this way, the veterinarian can be accompanied by this expert during the consultation while having his hands free to perform the manipulations that are necessary for this consultation or to interact with the mobile terminal. Additionally, the use of the mobile terminal and the questionnaire allows a precise approach to be followed, in particular according to different scenarios, each adapted to a given situation, in order to refine the evaluation or to specify the suspicions of disease. This questionnaire, filled out by the veterinarian and with the assistance of the remote expert, thus makes it possible to guide and facilitate the consultation in order to identify key points during the visit. It should be noted that, unlike a remote consultation, the system according to the invention allows the veterinarian in situ to maintain his role with regard to the farmers and therefore to maintain a trusting relationship with them. On completion of the questionnaire, the comment(s) generated by the controller of the mobile terminal allow the veterinarian to end the visit with a visit or check-up report or with a diagnosis that he establishes based on this or these comments. Of course, this report may be a preliminary report that can be enriched, by the veterinarian via the mobile terminal or by the expert remotely, by data derived from analyses of samples carried out subsequent to the visit, by additional information, by additional analyses or by proposed responses or treatments. Likewise, one or more additional visits may also make it possible to enrich this report, in an iterative manner, in order to arrive at a final report.

According to the invention, a mobile terminal is understood to mean a portable computer, a mobile device, a smart phone or an electronic tablet. This mobile terminal comprises various hardware components, including one or more processors with one or more cores and a memory.

If necessary, the controller of said mobile terminal may comprise all or part of said hardware components, as well as software components. Preferably, the controller of said mobile terminal may comprise a software application, for example downloaded into a memory of the mobile terminal and able to control the various elements of the mobile terminal, and in particular the display of the mobile terminal, for example based on the data entered via the interface. Alternatively, said software application may be partially downloaded into a memory of the mobile terminal and partially hosted on a remote server. In other cases, the software application may be partially or totally virtualized via a cloud architecture.

The term "interface of the mobile terminal" is understood to mean a data input interface, for example a touch interface, a voice interface or a gestural interface.

Connected device is also understood to mean worn on the head of a veterinarian, a helmet, a headband, a spectacles accessory or even a pair of spectacles provided or not with protective lenses. If necessary, the connected device may be a multimedia device, in particular in augmented reality.

Advantageously, the mobile terminal comprises a memory wherein a plurality of predetermined questions are stored, the questionnaire being formed by a sequence of questions selected from said plurality of questions and ordered according to a determined order. If necessary, the controller can be arranged to display, on the display of the mobile terminal, sequentially according to said determined order, question blocks comprising at least one question of said sequence as well as, for each question of said block, a graphical component for responding to said question. The term "graphical response component" is understood to mean a graphical interface component with which the veterinarian can interact, via the interface, to respond to a question, and in particular one of the following components or a combination of several of the following elements: a button, a drop-down list, a check box, a text entry area. In other words, the controller can be arranged, in response to an interaction of the veterinarian with a graphical response component via the interface, to record in said memory the response provided to the question associated with said graphical response component via this graphical response component.

For example, said plurality of predetermined questions can be stored in said memory as predetermined question groups. If desired, each question can be stored in the memory by being associated with an index, each group being formed by questions of the same index, said question blocks being formed from questions belonging to the same group. If necessary, the same group can provide questions to different blocks. Alternatively, said question blocks can be formed from questions belonging to different groups. For example, each question group can be a group of questions associated with an index indicating one of the following topics: epidemiology, zootechnical parameters and rearing techniques, biosafety, management, consultation, autopilot, sampling, immunization, history, analysis.

Preferably, the controller can be arranged to display, on the display of the mobile terminal, a graphical control component, and can be arranged, in response to an interaction of the veterinarian with said graphical control component via the interface, to display the following question block according to said determined order.

Advantageously, the controller can be arranged to display, on the display of the mobile terminal, an interface for selecting an input gate from a plurality of predetermined input gates and for selecting a sequence of questions from a plurality of predetermined questions according to the selected input gate, said sequence of selected questions forming said questionnaire. In other words, for two distinct input gates, questions may be different from one sequence to another and/or displayed in a different order from one sequence to another. For example, each input gate may be one of the topics: suspected failure of a vaccination campaign, respiratory epidemic, laboratory diagnosis, epidemiological investigation, sensitization to diseases, evaluation of a vaccination program, follow-up, innovation. Each input gate may, for example, be followed by a secondary input gate, in particular chosen from the following sub-topics: suspected Newcastle disease, suspected infectious bronchitis, suspected infectious laryngotracheitis, suspected infectious bursal disease, suspected avian flu.

Alternatively, the controller may be arranged to select a plurality of questions from a plurality of predetermined questions based on the selected input gate, said sequence of selected questions forming a question block. If applicable, the controller can be arranged to select a new plurality of questions from a plurality of predetermined questions based on the responses to said question block, said new selected question sequence forming a new question block, these steps being repeated until the controller selects a plurality of final questions forming a terminal question block, all of the successive question blocks forming said questionnaire.

In one embodiment of the invention, for at least one, in particular each, of said questions of said sequence, the controller is arranged to determine a response score based on the response provided to said question, and to generate said comment relative to the consultation based on at least one of said determined scores. For example, all the responses that can be given to each question may be predefined and stored in said memory of the mobile terminal, each of these responses being stored in said memory by being associated with a predetermined score. Alternatively or additionally, each question of said sequence may be subject to a quantifiable response, so that a score can be calculated by the controller from this response, for example by comparing said response to one or more thresholds.

Advantageously, a plurality of predetermined comments are stored in the memory of the mobile terminal. If necessary, the controller may be arranged to perform a comparison of at least one of said determined scores, or a comparison of a combination, in particular of a sum, of several of said determined scores, to one or more threshold values and to select one comment from said plurality of comments based on the result of said comparison.

Advantageously, for each question block, the controller is arranged to generate a comment relative to the consultation based on at least one score determined based on a response provided to one of the questions of said block. In other words, the controller will generate at least as many comments as the questionnaire comprises blocks.

According to one example embodiment of the invention, for at least one question block, the controller is arranged to display only part of the questions of this block, called preliminary part, and to display the rest of the questions of this block based on at least one score determined based on a response provided to one of the questions of said preliminary part. It is thus possible to simplify filling out the questionnaire by the veterinarian by avoiding the display of questions that are not relevant. According to yet another example, for at least one question block, the controller is arranged to display only some of the questions in this block, based on at least one response provided to one of the questions in a previous question block.

Advantageously, when the veterinarian has finished filling out the questionnaire, the controller is arranged to display, on the display of the mobile terminal, the set of comments relative to the consultation generated by the controller at the end of filling out of the questionnaire, as well as a set of graphical selection components each associated with one of the displayed comments, the controller being arranged to generate a consultation report containing the comments relative to the consultation, selected by means of said graphical selection components. For example, the controller may be arranged to authorize the selection of a predetermined number of comments. In this example, each predetermined comment stored in the memory of the mobile terminal may be associated with a comment category chosen from a list of predetermined categories. If necessary, the controller may be arranged to display said generated comments in a grouped and ordered manner according to their associated categories.

In one embodiment of the invention, the controller of said mobile terminal can be arranged, in response to a predetermined veterinarian interaction with the interface, such as, for example, a button press, to display, on the display of the mobile terminal, a graphical component for organizing a visit to a farm, in particular comprising a graphical sub-component intended for identifying a farm to be visited and/or a graphical sub-component of the calendar type.

In one embodiment of the invention, the controller of said mobile terminal can be arranged, in response to a predetermined veterinarian interaction with the interface, such as, for example, a button press, to display, on the display of the mobile terminal, a graphical component for reserving a remote expert. If applicable, the controller of said mobile terminal can be arranged to send a reservation email to said remote expert identified in said graphical reservation component and/or to reserve a time in a calendar of said remote expert identified in said graphical reservation component.

In one embodiment of the invention, the controller of said mobile terminal can be arranged, in response to a predetermined veterinarian interaction with the interface, such as, for example, a button press, to display, on the display of the mobile terminal, a graphical component for entering data relative to an animal vaccination campaign on said farm.

In one embodiment of the invention, the connected device is a pair of spectacles comprising a wireless communication module, a video acquisition system and a display, the system comprising a remote computing unit equipped with a system for acquiring and emitting audio, a display and a wireless communication module able to communicate with the wireless communication module of the connected device. According to this feature, the remote computing unit is intended to be used by the remote expert to communicate orally with veterinarian and to view, by means of the remote computing unit display, the visit and the various actions of the veterinarian, such as an autopsy, for example.

If necessary, the wireless communication module of the pair of spectacles can be arranged to transmit audio and/or video signals, acquired by the audio acquisition system and/or the video acquisition system of the connected device, to the wireless communication module of the remote computing unit, or to receive audio signals, acquired by the audio acquisition system of the remote computing unit, from the wireless communication module of the remote computing unit. For example, the wireless communication module of the pair of spectacles can be arranged to communicate with a telecommunication network, in particular a telecommunication network of the LTE type, for example 4th or 5th generation, of the Wi-Fi type, or of the Bluetooth type. Preferably, the video acquisition system of the pair of spectacles is a camera.

Advantageously, the wireless communication module of the pair of spectacles is arranged to transmit the images acquired by the video acquisition system of the pair of spectacles to the wireless communication module of the computing unit, the computing unit being arranged to display the received images on the display of the computing unit. If necessary, the computing unit comprises an interface for modifying at least one of said received images, and the computing unit is arranged to transmit an image modified by means of said modification interface to the wireless communication module of the pair of spectacles, via its own wireless communication module, the pair of spectacles being arranged to display said modified image on the display of the pair of spectacles. According to this feature, it is possible for the expert to take a screen capture in the visual broadcast of the veterinarian's visit on the display of the computing unit, for example during an autopsy or an observation of an area of the farm, and then to modify the image obtained via the modification interface, and to retransmit this modified image to the veterinarian via the display of the pair of spectacles in order to show him a point of interest. Modifying an image is understood in particular to mean one of the following modifications or a combination of several of the following modifications: magnification, addition of an arrow, circle or text to the image.

The invention also relates to a method for assisting a veterinary evaluation procedure implemented by a mobile terminal of a consultation system according to the invention.

In one embodiment, the method comprises the following steps:

a. Selecting, in a memory of the mobile terminal, a sequence of questions from a plurality of predetermined questions;

b. Sequentially displaying, on the display of the mobile terminal, question blocks each comprising at least one question of said sequence and, for each question of each block, a graphical response component to said question;

c. Generating at least one comment relative to said consultation depending on at least one of the responses given to the questions of said question sequence via the interface of the mobile terminal.

Preferably, said sequence of selected questions is ordered according to a determined order, beforehand or dynamically. For each question block, the display step may comprise displaying a graphical control component, so that an interaction, via the interface, with this graphical control component causes the display, instead of the current question block, of the following question block, that is, the question block comprising the questions of the sequence of questions succeeding the questions of the current question block according to said determined order.

Advantageously, the method comprises a prior step of displaying, on the display of the mobile terminal, an interface for selecting an input gate from a plurality of predetermined input gates stored in said memory, said sequence of questions being selected based on said input gate selected via the interface.

Advantageously, the method comprises, for each question block displayed on the display of the mobile terminal, a step of determining at least one response score to one of the questions of said question block based on the response given to said question using the interface. If necessary, said at least one comment relative to the consultation is generated based on at least one of the determined response scores. Preferably, the generating step comprises, for each question block, generating at least one comment relative to the consultation, based on at least one of the response scores determined from the response given to one of the questions in this question block.

Advantageously, for at least one question of at least one of the question blocks, in particular each of the question blocks, the graphical response component to said question displayed on the display of the mobile terminal is a selection component for selecting, via the interface, a response from a plurality of predetermined responses to said question, said responses being stored in said memory of the mobile terminal by being associated with a predetermined score. If appropriate, the response score that is determined from the response given to said question is the score associated with the response selected via the interface. Said selection component may for example be a plurality of buttons each indicating one of the predetermined responses or alternatively a drop-down list whereof each item is one of the predetermined responses.

Alternatively or additionally, for at least one question of at least one of the question blocks, in particular each of the question blocks, the graphical response component to said question displayed on the display of the mobile terminal is a component for entering a quantifiable response, for example a number, via the interface. If necessary, the response score determined from the response given to said question is calculated based on the response entered via the interface, for example by comparing said number with one or more thresholds.

Preferably, a plurality of predetermined comments are stored in said memory of the mobile terminal. If necessary, the step of generating said at least one comment relative to the consultation, based on at least one response given to one of the questions of said sequence of questions, comprises comparing the response score determined from said response to one or more threshold values, and selecting one comment from said plurality of predetermined comments based on the result of said comparison. Optionally, said comment may be selected based on the result of a comparison of a combination, in particular of a sum, of several scores determined from the responses given to various questions of a same question block, to one or more threshold values. Preferably, each predetermined comment of a group of comments may be associated, in said memory of the terminal, with a predetermined result of a comparison.

Advantageously, for at least one of the question blocks, the display step may comprise displaying only part of the questions of this block, called the preliminary part, determining at least one response score to one of the questions of said preliminary part based on the response given to said question using the interface, and, based on a comparison of said response score to one or several threshold values, displaying the rest of the questions of this block.

Advantageously, at the end of the step of generating at least one comment relative to said consultation, the method comprises a step of displaying, on the display of the mobile terminal, the set of comments generated relative to the consultation, as well as a set of graphical selection components each associated with one of the comments displayed. If necessary, the method may comprise a subsequent step of generating a consultation report containing the comments relative to the consultation selected by means of said graphical selection components via the interface.

The invention also relates to a computer program comprising a program code which is designed to implement the method according to the invention when said program is executed by a computer.

BRIEF DESCRIPTION OF THE DRAWINGS

The present invention is now described with the aid of purely illustrative examples which in no way limit the scope of the invention, and from the appended drawings, in which drawings the various figures show:

FIG. 1 shows, partially and schematically, a veterinary consultation system according to an example embodiment of the invention;

FIG. 2 shows, partially and schematically, an image acquired by the camera of the pair of spectacles of the consultation system of [FIG. 1], modified by the remote expert and transmitted to the display of the pair of spectacles, during another step of the method of [FIG. 2];

FIG. 3 shows, partially and schematically, a method for assisting with a consultation implemented by the mobile terminal of the consultation system of [FIG. 1]; and FIG. 4 shows, partially and schematically, a view of the display of the mobile terminal of the consultation system of [FIG. 1] during a step of the method of [FIG. 3];

FIG. 5 shows, partially and schematically, a view of the display of the mobile terminal of the consultation system of [FIG. 1] during another step of the method of [FIG. 3];

FIG. 6 shows, partially and schematically, a view of the display of the mobile terminal of the consultation system of [FIG. 1] during another step of the method of [FIG. 3];

FIG. 7 shows, partially and schematically, a view of the display of the mobile terminal of the consultation system of [FIG. 1] during another step of the method of [FIG. 3];

FIG. 8 shows, partially and schematically, a view of the display of the mobile terminal of the consultation system of [FIG. 1] during another step of the method of [FIG. 3]; and FIG. 9 shows, partially and schematically, a view of the display of the mobile terminal of the consultation system of [FIG. 1] during another step of the method of [FIG. 3].

DETAILED DESCRIPTION OF THE INVENTION

In the following description, identical elements, by structure or function, appearing in different figures, retain the same references unless otherwise specified.

A veterinary consultation system 1 has been described in [FIG. 1], in particular intended for a consultation of a poultry farm or a hatchery or a slaughterhouse. In the example which will be described, the system 1 is intended to be used, on the one hand, by a veterinarian visiting the poultry farm or the hatchery, for diagnostic, evaluation or check-up purposes, and on the other hand, by a remote veterinary expert, having a set of skills specific to the poultry of this poultry farm, such as for example skills relating to the diagnosis of diseases likely to contaminate them and to treatments or vaccines for treating these diseases.

The system 1 comprises a connected device 2, shown in this example in the form of a pair of spectacles 2 equipped with arms 21 to allow it to be held on the veterinarian's head. In the example described, the pair of spectacles 2 has no protective lenses, but has a bridge located between the arms and intended to rest on the veterinarian's nose, the space between the bridge and the arms being able to receive protective lenses. Alternatively, it would be possible to envisage replacing the arms 21 with a strip or any other means for holding the connected device 2 on the veterinarian's head.

The pair of spectacles 2 comprises a module 22 mounted on one of the arms 21. The pair of spectacles 2 comprises a system for acquiring and emitting audio comprising a speaker 23, arranged on the arm 21 opposite that receiving the module 22 and intended to come opposite the veterinarian's ear, and a microphone 24, provided on a wing of the module 22. The pair of spectacles 2 comprises a camera 25, arranged on the wing of the module 22, in line with the microphone 24, as well as a display 26, arranged on the opposite face of the wing of the module 22 receiving the camera 25 and the microphone 24 so as to face the veterinarian's eye.

The module 22 further carries a wireless communication module 27, able to transmit data frames according to a Wi-Fi protocol and/or a Bluetooth protocol, as well as a battery (not shown) intended to power the set of electronic elements of the pair of spectacles 2 and a plurality of buttons and/or touch interfaces intended to control these various electronic elements.

The system 1 also comprises a mobile terminal 3, shown in this example in the form of a touch tablet 3, intended to equip the veterinarian wearing the pair of spectacles 2.

The touch tablet 3 is equipped with a touch screen 31, forming both a display and an input interface, and with a set of electronic components 32 comprising in particular a processor and thus a memory 33. A software application A is stored in the memory 33 and is able to control the display of various graphical components on the touch screen 31, in particular based on interactions by the veterinarian with the touch screen 31, such as taps or holds, swipes or data entries. The application A thus forms part of a controller of the touch tablet 3.

The touch tablet 3 also comprises a wireless communication module 34, able to transmit data frames according to an LTE protocol and/or a Wi-Fi protocol and/or a Bluetooth protocol, as well as a battery (not shown) intended to power all of the electronic elements of the touch tablet 3.

The system 1 also comprises a remote computing unit 4, intended to be handled by the veterinarian's remote expert, shown in this example in the form of a laptop computer 4.

The laptop computer 4 comprises a system for acquiring and emitting audio 41, in the form of a microphone and a speaker, a display 42, an interface 43, in the form of a keyboard and a touchpad, and a wireless communication module 44, able to transmit data frames according to an LTE protocol and/or a Wi-Fi protocol and/or a Bluetooth protocol In the example described, the pair of spectacles 2 is connected, by Bluetooth link, with the touch tablet 3. The pair of spectacles 2 can thus exchange audio and video signals with the laptop computer 4, either directly by Wi-Fi link via their communication modules 27 and 44, or via the touch tablet 3, the signals being exchanged between the pair of spectacles 2 and the touch tablet 3 by Bluetooth link and between the touch tablet 3 and the laptop computer 4 by LTE or Wi-Fi link. In this way, the veterinarian and the remote expert can communicate orally, via the systems for acquiring and emitting audio 23/24 and 41. Moreover, the remote expert can follow the veterinarian's visit on the display 42, since the images acquired by the camera 25 of the pair of spectacles are retransmitted. Additionally, the remote expert is thus able to take a screen capture in this broadcast, modify the image captured by means of the interface 43, for example by inserting a circle or an arrow therein as shown in [FIG. 2], then transmit this modified image to the pair of spectacles 2 so that it is displayed on the display 26.

We will now describe in [FIG. 3] an example of a method implemented by the software application A during the consultation carried out by the veterinarian on the poultry farm or at the hatchery that he is visiting, the software application controlling the display 31 of the tablet 3, in particular based on the interactions of the veterinarian with the tablet. [FIG. 2] will subsequently be described in connection with [FIG. 4] to [FIG. 9], which show the display 31 of the touch tablet 3 in different steps of the method of [FIG. 3].

Prior to the visit, the veterinarian can access a sheet of the application A, called visit manager, allowing organization of his visits. In a step E01, following an interaction of the veterinarian, via the display 31, with a graphical control component displayed on the display 31 and dedicated to this visit manager (not shown), the application A controls the display 31 so as to display said visit manager thereupon. If necessary, said manager may comprise a list of all the visits planned or carried out by the veterinarian, as well as a graphical component for creating a new visit.

In a step E02, following an interaction of the veterinarian, via the display 31, with this graphical component for creating a new visit, the application A controls the display 31 so as to display a page for creating a new visit, shown in [FIG. 4]. This page comprises a plurality of graphical components, including at least one graphical component A01 intended for identifying a poultry farm to be visited, a graphical component for reserving an expert A02, and a graphical component of the calendar type A03. In the example described, component A01 is a text input area and component A03 is a calendar wherein it is possible to reserve a time slot.

The graphical reservation component for reserving an expert A02 may be a drop-down list, whereof each item indicates the name of an available expert, for example chosen from a list of predetermined experts. The application A may for example obtain said list of experts by querying a remote database, depending on a visit time H entered by the veterinarian, via the component 103. Components A01 to 103 have been shown in [FIG. 3] by being displayed on the same page, it being understood that they may be displayed on different tabs of a same page, and that this page may comprise other components not shown in [FIG. 3], in particular components for identifying the address of the poultry farm, identifying the name of the farmer, and inputting data relative to a vaccination program of the poultry from this poultry farm.

It should be noted that a graphical component T, in the form of a button, makes it possible to trigger a call between the veterinarian and the expert. For example, following an interaction of the veterinarian with this component, the application A transmits a call instruction to the pair of spectacles 2, the pair of spectacles 2 being arranged, upon receipt of this call instruction, to initiate an exchange of audio and/or video signals between said pair of spectacles 2 and the laptop computer 4.

At the beginning of his visit to the poultry farm, the veterinarian can initialize the display of a questionnaire. In a step E11, following an interaction with the veterinarian, via the display 31, with a graphical control component displayed on the display 31 and dedicated to this questionnaire (not shown), the application A controls the display 31 to display an interface therein for selecting an input gate from among a plurality of predetermined input gates, shown in [FIG. 5].

This interface comprises a plurality of graphical selection components A1*i*, in this case buttons A11 and A12, each indicating a topic such as, for example, "suspected failure of a vaccination campaign" and "respiratory epidemic." Each of these topics is stored in the memory 33 of the tablet 3 and is thus displayed on the display 31, in the form of a graphical selection component A11 or A12, by the application A.

In a step E12, following an interaction with the veterinarian, via the display 31, with one of the graphical selection components A1*i*, the application A controls the display 31 so as to display a plurality of additional graphical selection components A1*ij* thereupon, in this case buttons A111 to A114, each defining a predetermined input gate, such as for example one of the following sub-topics: suspected Newcastle disease, suspected infectious bronchitis, suspected infectious laryngotracheitis, suspected infectious bursal disease. A plurality of sub-topics is stored in the memory 33 of the tablet 3, each sub-topic being associated with one of the topics stored in this memory 33. Therefore, the selection by the veterinarian of one of the topics, by means of the buttons A1$i$, allows the application A to identify, in the memory 33, the sub-topics associated with the selected topic and to display them, on the display 31, in the form of graphical selection components A1$ij$, so that the veterinarian can select one of these sub-topics as an input gate of the questionnaire.

A plurality of predetermined questions QI is stored in the memory 33 of the touch tablet 3, the questions QI being associated with an index m so as to be able to be grouped into a group of questions Gm of a same index m. The questions QI of a same group Gm may for example be questions relative to the same subject, such as for example epidemiology, management of the poultry farm, the history of the poultry farm, the vaccination program followed, biosafety, the consultation or the autopsy.

Following the veterinarian's selection, via the display 31, of an input gate A1$ij$, the application A selects, in a step E21, a sequence Sij of questions in the memory 33 and from the questions QI, said sequence having been defined beforehand and ordered according to a determined order. It should be noted that the sequence Sij selected from one of the input gates A1$ij$ will be different from the sequence Sik selected from another input gate A1$ik$, the questions of the sequence Sij being able to be different from those of the sequence Sik, and/or identical to those of the sequence Sik but ordered according to a different order. In the example described, the beginning of the sequence S13 that has been selected, following the selection of input gate A113 by the veterinarian, is formed by questions Q1 to Q4 of group G1, questions Q5 and Q6 of group G2 and question G7 of group G3.

Figure 6:
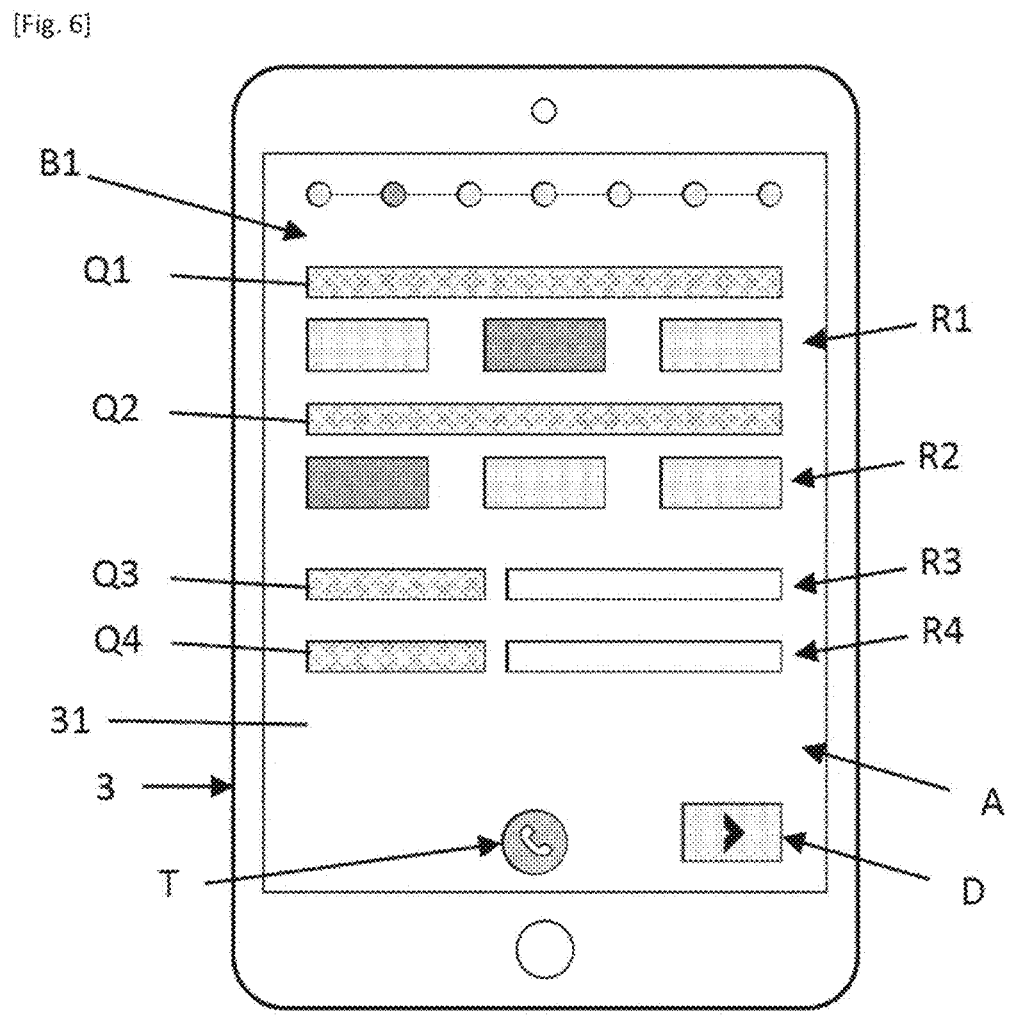

In a step E22, the application A displays, on the display 31, the questions QI of the selected sequence Sij by grouping them together by question blocks Bn displayed sequentially according to the order of the selected sequence. [FIG. 6] and [FIG. 7] each show the display of the block B1, respectively B2, on the display 31.

In the example described, each question block Bn can be formed by questions QI, or even all the questions, of a same group of questions Gm, as in the case of the block B1 formed by questions Q1 to Q4 of group G1, or by questions from different groups, as in the case of block B2, formed by questions Q5 and Q6 of group G2 and question G7 of group G3.

For each block Bn, the application A thus displays, on the display 31, the set of questions QI of this block Bn, as well as, for each question QI of this block Bn, one or more graphical response components RI to this question. The type of graphical response component to a given question is predetermined and associated with this question. For example, for a given question QI, several possible responses can be given. Each of these possible responses can thus be displayed by the application A on the display 31, in the form of a button, all of these buttons forming the graphical response component, as for questions Q1, Q2 and Q5 to Q7. According to another example, the graphical response component may be a number entry area, as in the case of questions Q3 and Q4.

In the example described, a single block Bn can be displayed each on the page of the application A and a graphical control component D is provided for scrolling the blocks Bn in the determined order of the sequence of questions. In other words, the questions and the blocks are organized logically according to the goal sought by the consultation, this goal being identified by means of the input gate. In the example described, if the selected input gate is suspected Newcastle disease, the goal of block B1 may have the aim of collecting epidemiological data and the questions of block B2 may have the aim of collecting biological analysis data, while the questions of the following blocks may have the aim of collecting environmental data, clinical data, data relating to the management of the poultry farm, etc. The veterinarian is thus guided in his consultation, owing to the questionnaire and with the support of the remote expert, if necessary.

For each question QI, the response given by the veterinarian, via the graphical response component RI, is recorded by the application A in the memory 33 of the tablet 3.

In a step E23, when filling out of the questionnaire is complete, indicated for example by an interaction of the veterinarian with a dedicated graphical control component, the application A determines, for each question block Bn, a response score SI to at least one of the questions QI of this block Bn, based on the response given by the veterinarian to this question via the graphical response component RI.

For example, when the graphical response component RI allows the veterinarian to select a response from several possible responses, each possible response can be stored in the memory 33 of the mobile tablet by being associated with a given score. The selection of a response thus allows the application A to assign the associated score to this response. When the graphical response component RI allows the veterinarian to enter a number, this number can be compared to one or more thresholds, the result of this comparison allowing the application A to assign a score to the response.

A plurality of consultation comments Cp are stored in the memory 33 of the mobile tablet 3. In a step E31, the application A compares one of the scores SI, several of the scores SI, or even each score SI determined at the end of step E23, or one or several combinations of these scores SI, for example of the sums of these scores SI, to one or more predetermined threshold values.

In a step E32, the application A selects at least one of the consultation comments Cp based on the result of one of these comparisons or of a logical combination of several comparisons. For example, several consultation comments Cp can be stored in the memory 33 of the touch tablet 3 by each being associated with a different result of a same comparison of a response score to one or more given threshold values. In the example described, the application A proceeds with a comparison of the response scores S1, S2 and S7, determined respectively from the responses R1, R2 and R7, to given threshold values to select the comments C1, C2 and C5, while it performs a comparison of the sum of the response scores S3 and S4, determined respectively from the responses R3 and R4, to given threshold values to select the comment C3 and performs a comparison of the sum of the response scores S5 and S6, determined respectively from the responses R5 and R6, to given threshold values to select the comment C4.

In a step E33, the application A displays, on the display 31, the comments Cp generated at the end of step E32, by grouping them together according to the question block Bn having enabled their selection, as shown in [FIG. 8].

The application A also displays, for each displayed comment Cp, a graphical selection component CB allowing the veterinarian to select or not select this comment.

In a step E4, at the end of the selection of the comments by the veterinarian, indicated for example by an interaction of the veterinarian with a dedicated graphical control component, the application A generates a consultation report containing these selected comments, as shown in [FIG. 9], as well as the set of responses given to the questions of the questionnaire, which will be used by the veterinarian to support his diagnosis or recommendations. This report may be a preliminary report that can be enriched, by the veterinarian via the mobile terminal or by the expert remotely, by data derived from analyses of samples carried out subsequent to the visit, by additional information, by additional analyses or by proposed responses or treatments. Likewise, one or more additional visits may also make it possible to enrich this report, in an iterative manner, in order to arrive at a final report.

The foregoing description clearly explains how the invention makes it possible to achieve the objectives that it set, namely to allow a veterinarian to carry out an in situ consultation on a farm and to conduct a check-up, evaluation or diagnosis in the fastest and most reliable manner possible, owing to the combination of a connected device enabling him to converse with a remote expert, which will provide him, in addition to his expertise, with the assurance of a holistic and relevant approach, and of a mobile terminal provided with a questionnaire making it possible to guide and facilitate the consultation, in order to identify key points during the visit.

In any case, the invention is not limited to the specific embodiments described in this document, and extends in particular to any equivalent means and to any technically operative combination of these means.

What is claimed is:

1. An interactive consultation system for assisting with a veterinary evaluation procedure, comprising:
   a. a wearable connected device, comprising a pair of spectacles, configured to be worn on the head of a veterinarian and comprising a video acquisition system, an audio acquisition and emission system, and a first wireless communication module;
   b. a mobile terminal comprising:
      i) a display;
      ii) a user interface;
      iii) a memory storing a plurality of predetermined questions;
      iv) a controller including a processor,
wherein the controller is configured to:
   select and determine an order of a sequence of questions from said plurality of questions to form a consultation questionnaire;
   display a consultation questionnaire in accordance with the determined order;
   receive responses provided via the user interface; and
   determine, based on at least one response, a response score; and generate at least one comment relative to the consultation questionnaire based on the response score, and wherein the controller is further configured to display this sequence of questions in the form of question blocks that are ordered according to said determined order, and for at least one of said question blocks, further configured to display only part of the questions, called preliminary part, and to display the rest of the questions of this question block based on at least one response score determined based on a response provided to one of the questions of said preliminary part,
   communicate, via said wireless communication module, with the wearable connected device to receive real-time video and audio data during the consultation;
   transmit, during the consultation, one or more images captured by the video acquisition system of the wearable connected device to a remote computing unit for review and annotation;

receive from the remote computing unit annotated images comprising at least one graphical overlay identifying a region of interest; and
   display the annotated images on the spectacles to guide the veterinarian during the evaluation procedure.

2. The interactive consultation system according to claim 1, wherein the controller is further configured to display, sequentially according to said determined order, said question blocks further comprising for each question of said block, a graphical response component to said question.

3. The interactive consultation system according to claim 2, wherein the controller is arranged to display, on the display of the mobile terminal, an interface for selecting an input gate from a plurality of predetermined input gates and for selecting a sequence of questions from a plurality of predetermined questions according to the selected input gate, said sequence of selected questions forming said questionnaire.

4. The interactive consultation system according to claim 1, wherein, for each question block, the controller is arranged to generate a comment relative to the consultation based on at least one score determined based on a response provided to one of the questions of said block.

5. The interactive consultation system according to claim 1, wherein, when the veterinarian has finished filling out the questionnaire, the controller is arranged to display, on the display of the mobile terminal, the set of comments relative to the consultation generated by the controller at the end of filling out of the questionnaire, as well as a set of graphical selection components each associated with one of the displayed comments, the controller being arranged to generate a consultation report containing the comments relative to the consultation, selected by means of said graphical selection components.

6. The system according to claim 1, wherein the wireless communication module of the pair of spectacles is arranged to transmit images acquired by the video acquisition system of the pair of spectacles to the wireless communication module of a computing unit, the computing unit being arranged to display the received images on the display of the computing unit, wherein the computing unit comprises an interface for modifying at least one of said received images, and wherein the computing unit is arranged to transmit an image modified by means of said modification interface to the wireless communication module of the pair of spectacles, via its own wireless communication module, the pair of spectacles being arranged to display said modified image on the display of the pair of spectacles.

7. A method for assisting with a consultation implemented by the interactive consultation system according to claim 1, comprising:
   receiving, at the mobile terminal, real-time video and/or audio data from the wearable connected device;
   transmitting, during the consultation, one or more images captured by the wearable connected device to a remote computing unit for annotation;
   receiving, from the remote computing unit, annotated images comprising at least one graphical overlay identifying a region of interest;
   displaying, on at least one of the wearable connected device and the mobile terminal, the annotated images to guide the veterinarian during the evaluation procedure;
   displaying, on the mobile terminal, a questionnaire as a sequence of question blocks, and dynamically selecting additional blocks or questions based on at least one response score or the received data; and generating comments and a consultation report incorpo-
rating at least a portion of the annotated images and the
responses to the questionnaire.

8. A non-transitory computer-readable medium compris-
ing instructions, that, when executed by a processor of a
mobile terminal of the interactive consultation system
according to claim 1, cause the processor to:

receive, from a wearable connected device comprising a
camera and a display, real-time video and/or audio data
captured during a veterinary consultation; transmit one or more captured images to a remote com-
puting unit for annotation;

receive from the remote computing unit annotated images
including at least one modification comprising an
arrow, circle, or text identifying a region of interest; display the annotated images on at least one of the
wearable connected device and the mobile terminal to
guide the veterinarian during the consultation;

display, on the mobile terminal, a questionnaire as a
sequence of question blocks, and dynamically select
additional blocks or questions based on at least one
response score or the received data; and generate comments and a consultation report incorporat-
ing at least a portion of the annotated images and the
responses to the questionnaire.

\*   \*   \*   \*   \*